(12) United States Patent
Curtis

(10) Patent No.: US 7,189,264 B2
(45) Date of Patent: Mar. 13, 2007

(54) LIMB WITH MODULAR PROSTHETIC COMPONENTS

(75) Inventor: Michael J. Curtis, Green Bay, WI (US)

(73) Assignee: American Prosthetic Components, Inc., Green Bay, WI (US)

( * ) Notice: Subject to any disclaimer, the term of this patent is extended or adjusted under 35 U.S.C. 154(b) by 229 days.

(21) Appl. No.: 10/768,887

(22) Filed: Feb. 2, 2004

(65) Prior Publication Data
US 2005/0171617 A1   Aug. 4, 2005

(51) Int. Cl.
*A61F 2/74* (2006.01)
(52) U.S. Cl. ...................................... 623/27
(58) Field of Classification Search .............. 623/27, 623/28, 33, 34, 39, 40, 43–45, 47–49, 53; 403/299, 301, 309, 313, 191, 196, 307, 43, 403/44, 46
See application file for complete search history.

(56) References Cited

U.S. PATENT DOCUMENTS

| 3,400,408 | A | * | 9/1968 | Garcia ........................ 623/43 |
| 3,906,552 | A | * | 9/1975 | Weber ......................... 623/47 |
| 3,947,897 | A | | 4/1976 | Owens |
| 4,564,365 | A | * | 1/1986 | Winer et al. .................. 623/27 |
| 5,303,611 | A | * | 4/1994 | Chi ............................ 74/551.1 |
| 5,454,281 | A | * | 10/1995 | Chi ............................ 74/551.1 |
| 5,490,537 | A | | 2/1996 | Hill |
| 5,540,457 | A | * | 7/1996 | Johnson ....................... 280/279 |
| 5,571,192 | A | | 11/1996 | Schonhoffer |
| 5,800,562 | A | * | 9/1998 | Wilkinson ..................... 623/27 |
| 5,984,972 | A | * | 11/1999 | Huston et al. ................. 623/35 |
| 6,051,026 | A | * | 4/2000 | Biedermann et al. .......... 623/38 |
| 6,318,741 | B1 | * | 11/2001 | Chen ........................ 280/87.041 |
| 6,322,092 | B1 | * | 11/2001 | Chen .......................... 280/279 |
| 6,692,533 | B2 | * | 2/2004 | Johnson et al. ............... 623/47 |
| 6,981,992 | B2 | * | 1/2006 | Curtis ......................... 623/33 |

FOREIGN PATENT DOCUMENTS

FR    2708848 A1    2/1995

* cited by examiner

*Primary Examiner*—Alvin J. Stewart
(74) *Attorney, Agent, or Firm*—Brannen Law Office, LLC

(57) ABSTRACT

The present invention relates to a system with modular components for forming a prosthetic limb, wherein the effective length of the limb is adjustable to accommodate changing needs of a particular person. Several modular components are provided, including sleeve and spacer modules. Each sleeve module has a body with a selected length and has two opposed ends that are internally threaded. Each spacer module has a body of a selected length and has two opposed ends that are externally threaded. The modules are usable with existing prosthetic components have respective mating ends. The modules are twistable with respect to each other, which enables the effective length of the prosthetic limb to be adjusted. Further, the modules can be interchanged with modules having a different length, which enables large adjustment capabilities. A fully custom fitted prosthetic limb is therefore achievable without the need to custom make a single component.

4 Claims, 16 Drawing Sheets

BACKGROUND MATERIAL

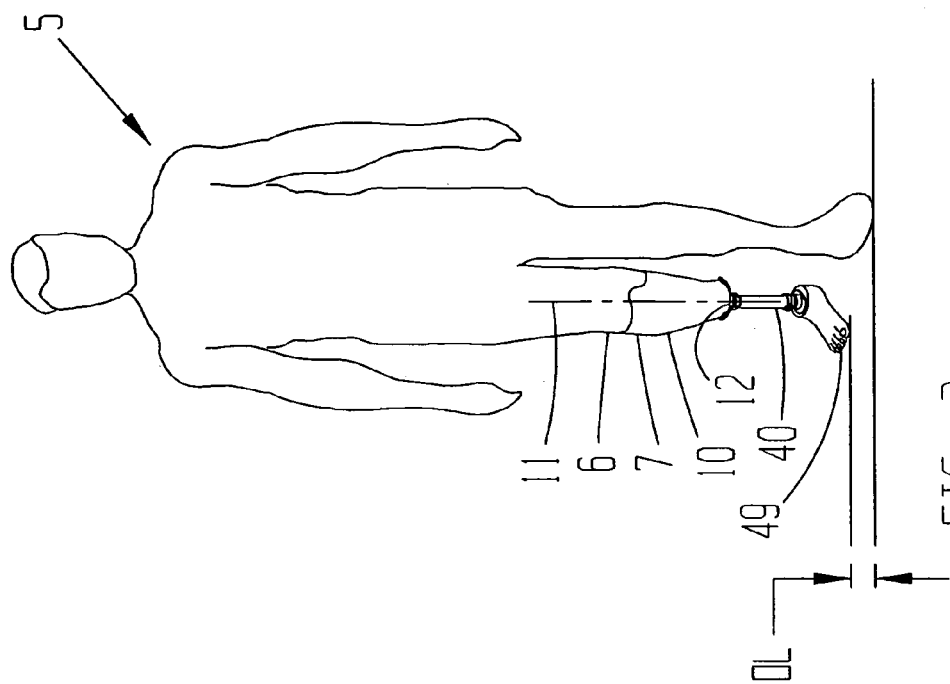
FIG. 2 BACKGROUND MATERIAL
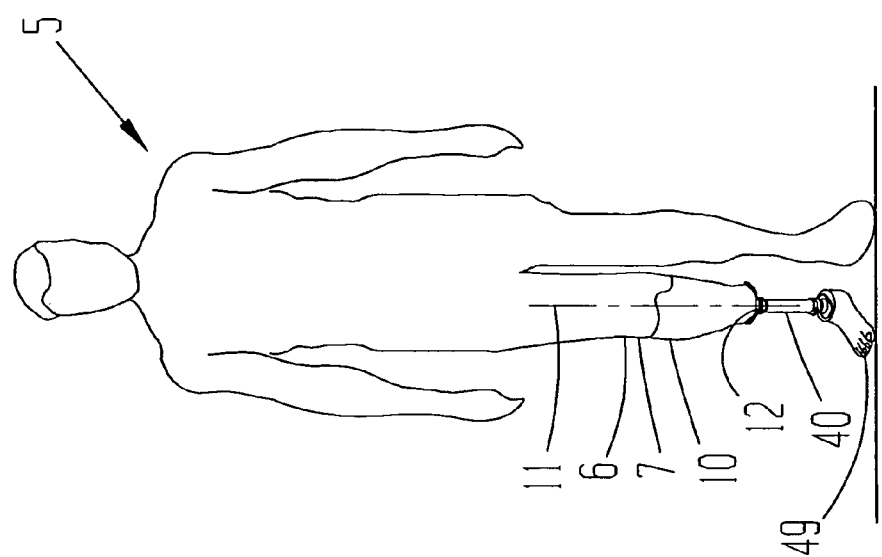
FIG. 3 BACKGROUND MATERIAL

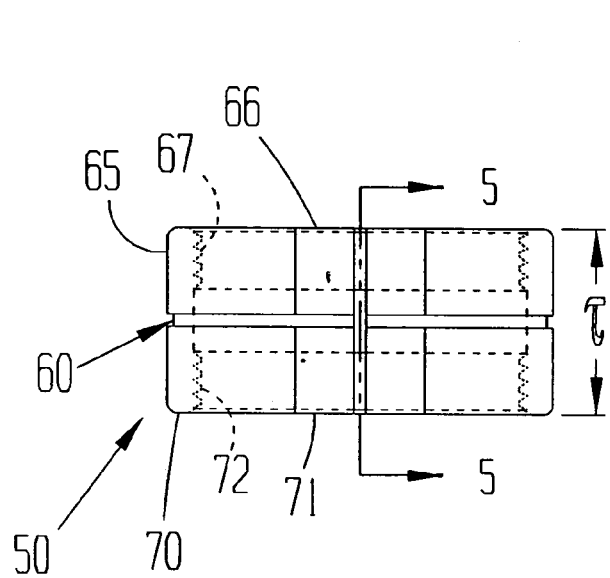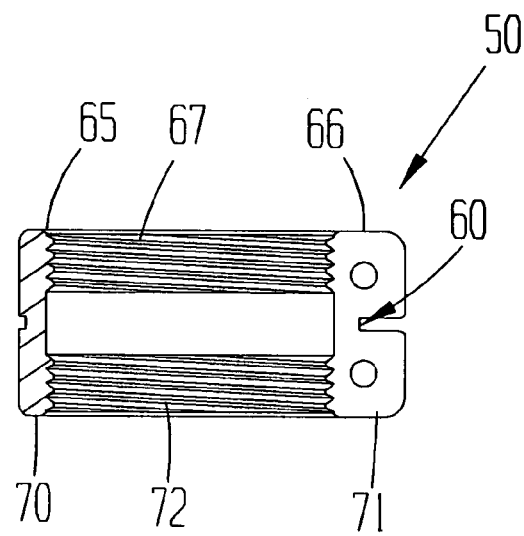
FIG. 4    FIG. 5
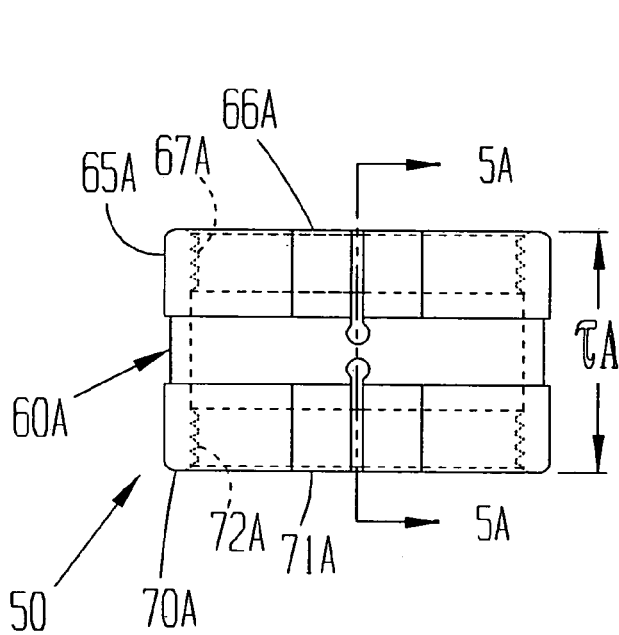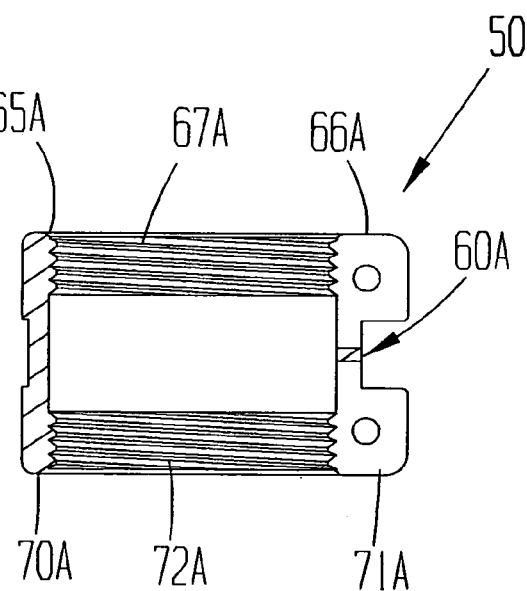
FIG. 4A    FIG. 5A

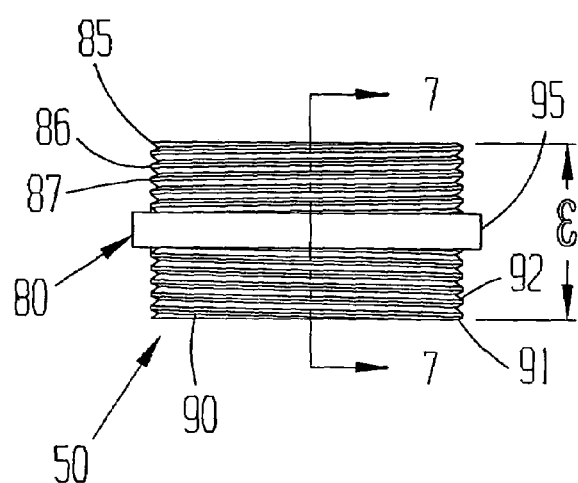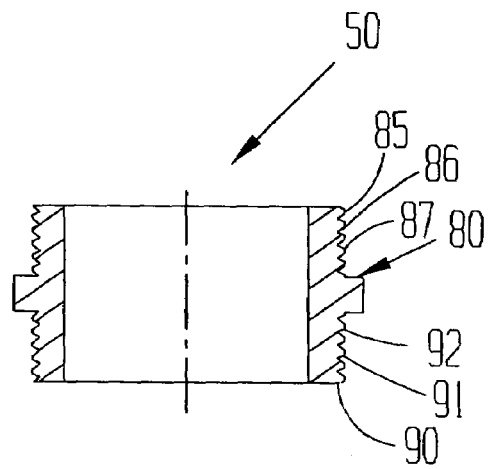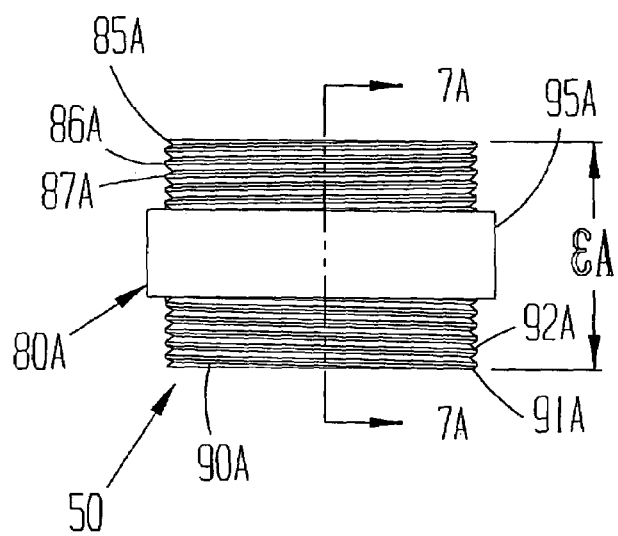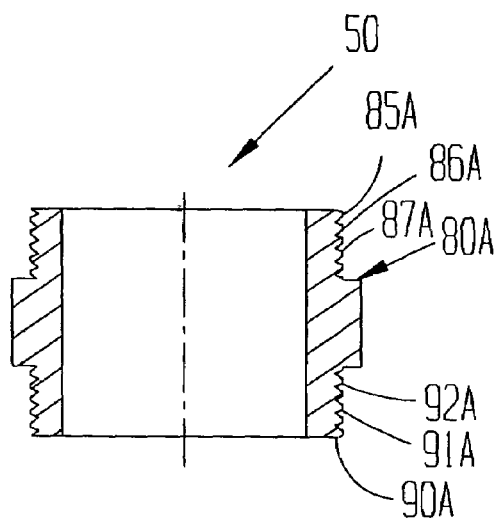
FIG. 6    FIG. 7
FIG. 6A   FIG. 7A

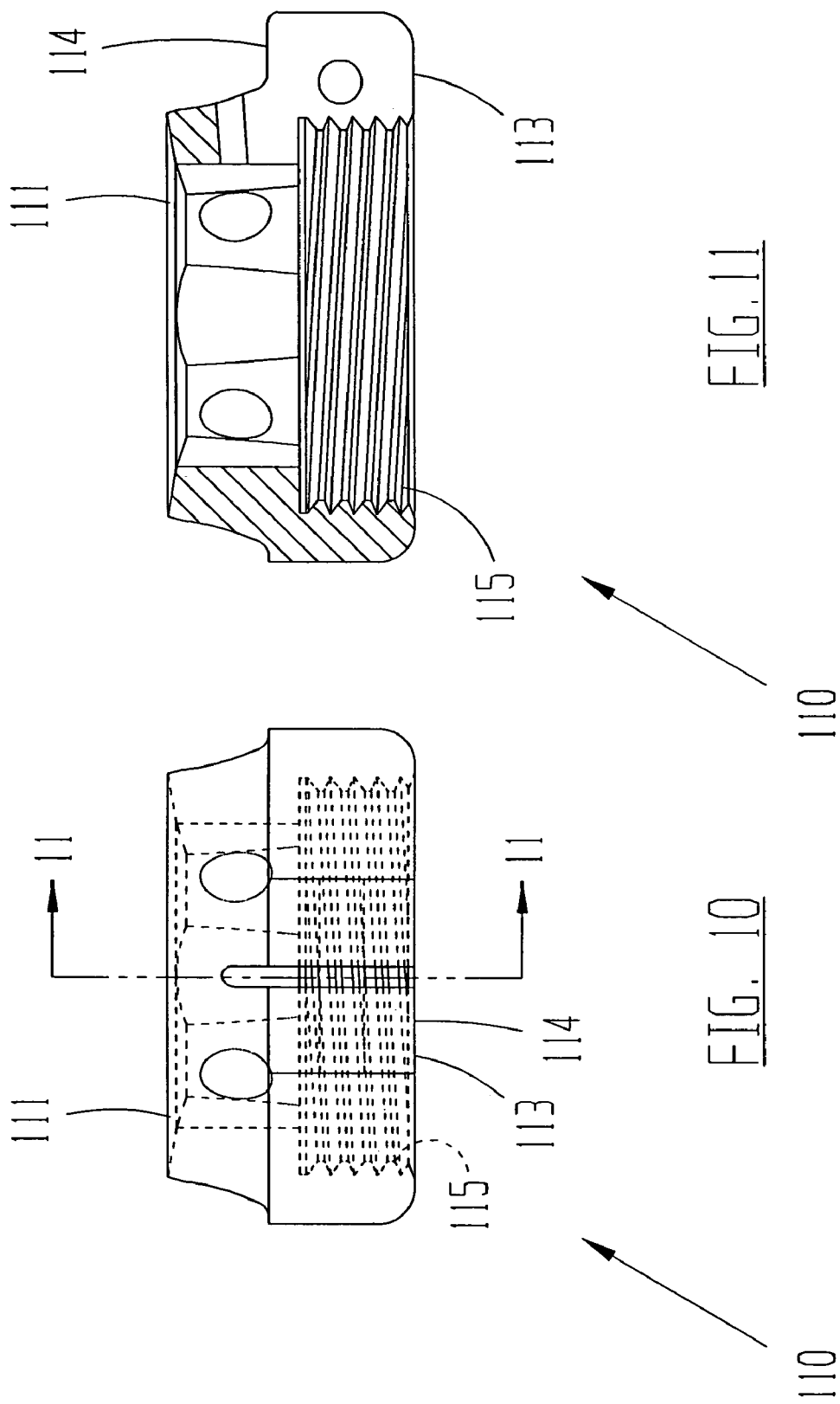

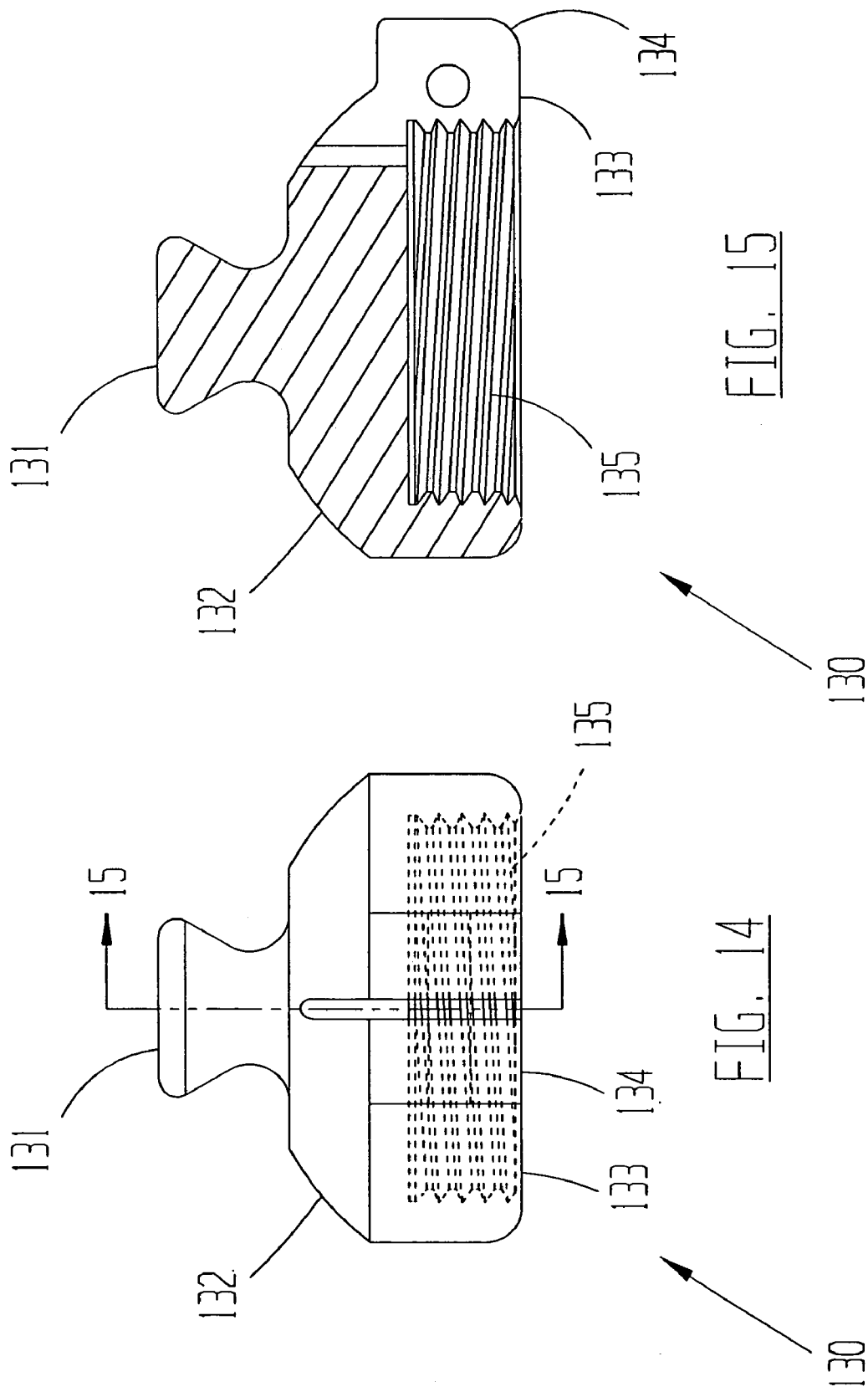

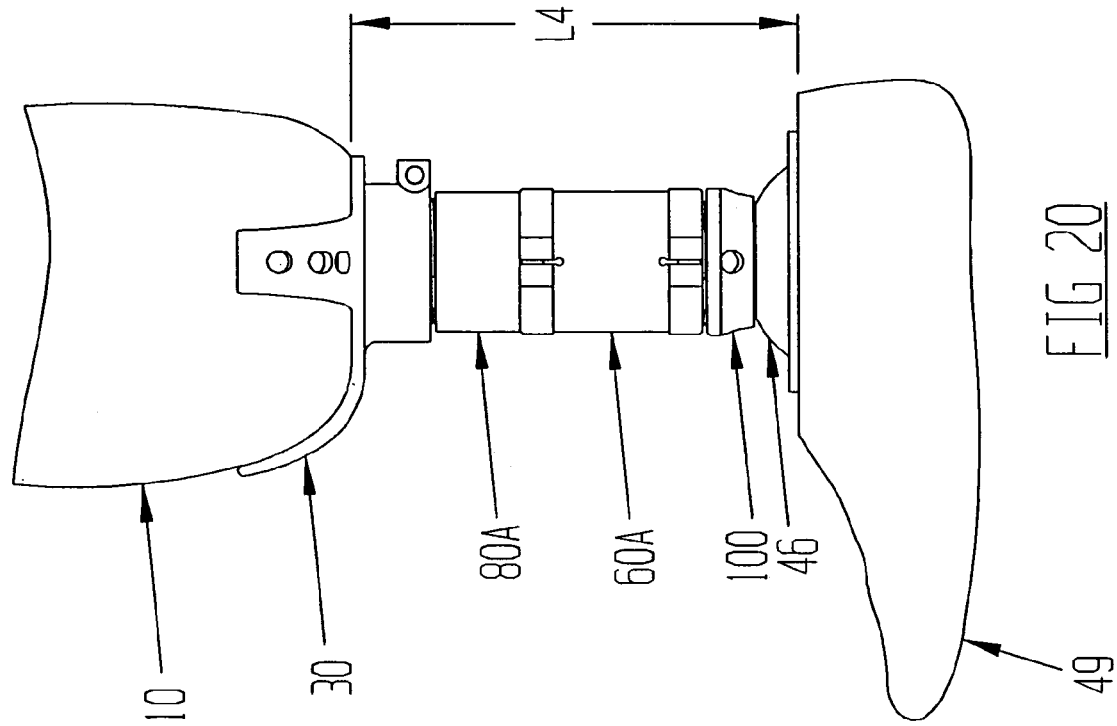
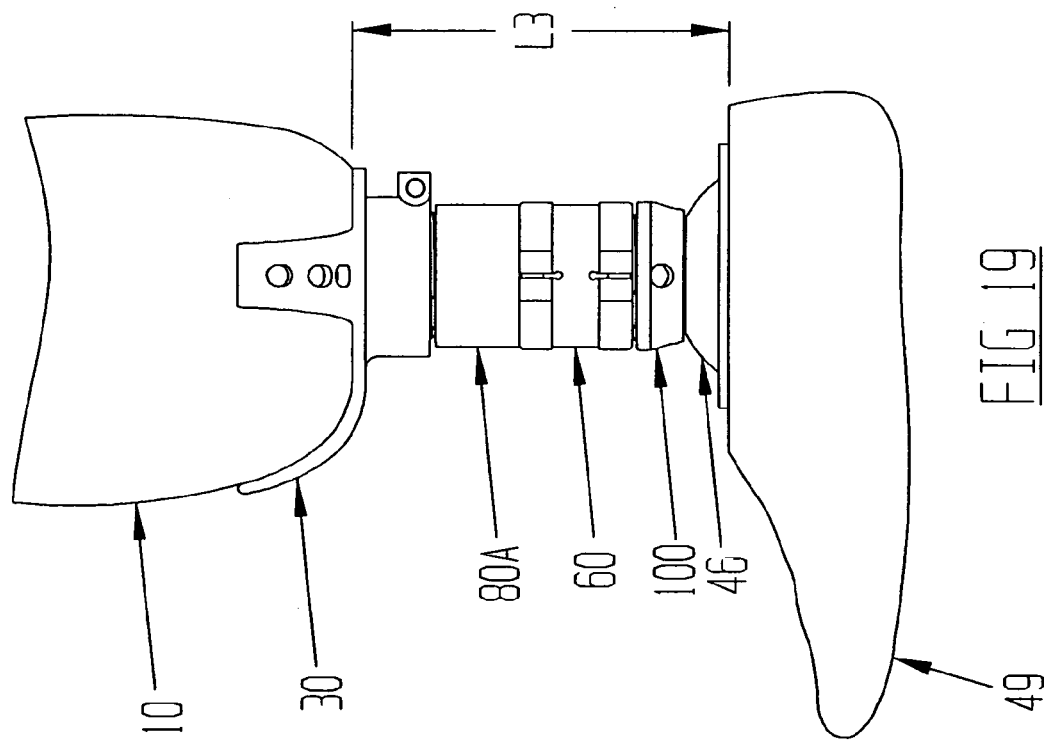

LIMB WITH MODULAR PROSTHETIC COMPONENTS

BACKGROUND OF THE INVENTION

1. Field of the Invention

The present invention relates to components for use in a modular prosthetic limb wherein the effective length of the limb is adjustable to suit the particular needs of a person as the person grows and/or shrinks due to age or any other reason.

2. Description of the Related Art

Sometimes, due to accidents, health problems, birth defects, etc., people 5 need to have a limb 6 amputated. The amputated limb 6 terminates in a stump 7. In general, a socket 10 can be formed for any particular stump 7. Those sockets 10 are well known in the art, and each socket 10 has a central axis 11 and an end 12.

Fortunately for people requiring a prosthetic limb, much advancement has been made in the field of prosthetic limbs. People now have many choices, including endoskeletal and exoskeletal prosthetic limbs. The present invention relates generally to endoskeletal prosthetic limbs. That is, limbs comprised of structural components and that may have an optional aesthetic outer shell.

One conventional and exemplary prosthetic limb setup is shown in FIG. 1. As shown, a conventional socket 10 is shown connected to a stump 7. The socket 10 has a socket central axis 11 and has an end 12. A three prong adapter 30 has a central axis and is shown to be connected to the socket 10. The three prong adapter 30 is capable of being connected to the socket 10 at a rotational angle relative to the three prong adapter central axis. Hence, the three prong adapter 30 can be positioned in any rotational orientation relative to the socket 10 in the lateral direction 15, the medial direction 16, the anterior direction 17 and the posterior direction 18. A pyramidal adapter 130 is shown connected to the three prong adapter 30. A pylon 40 with a fixed receiver 41 is shown connected to the pyramidal adapter 130. A tube clamp 43 is shown connected to the pylon 40. The pylon 40 must be fully received within the tube clamp 43 in order to be properly connected thereto. The tube clamp 43 has a pyramidal receiver 44 that connects to a foot adapter 46. The foot adapter 46, in turn, connects to a prosthetic foot 49.

This and other existing prosthetic limbs generally work quite well for their intended purposes. Yet, certain drawbacks and disadvantages can be associated with existing prosthetic limbs.

As a general matter, great skill is required to construct and assemble a prosthetic limb. As shown in FIG. 1, a prosthetic limb may involve several components. Yet, the components shown only comprise one set up. Many other components exist. The practitioner first has to select desired components from a multitude of component options. Next, the practitioner needs to determine the overall length and orientation of the prosthetic limb. This step involves selecting and sizing the components so that the prosthetic limb will have a length that is identical to that of the natural limb. Additionally, the practitioner will need to account for any angular and rotational adjustments that may be necessary to properly fit the prosthetic limb to the person.

Frequently, the practitioner decides to incorporate a pylon into the prosthetic limb. The practitioner can easily cut the pylon to a predetermined length using conventional methods. The cut end of the pylon can be connected to and secured in place with the clamp of an adjacent component. To accomplish this, the pylon must be fully received within the tube clamp and there is no ability to longitudinally adjust the pylon with respect to the tube clamp. One apparent drawback is that the pylon must be cut to an exact length in order for the overall length of the prosthetic limb to be correct. Yet, sometimes the practitioner miscalculates the amount of the pylon that needs to be cut off. In this case, the overall length of the prosthetic limb would be too long or too short. In the event that the overall prosthetic limb is too long, more of the pylon can be cut off to remedy the problem. Yet, if the pylon is cut too short, a new pylon will need to be cut in order to remedy the situation. Hence, the process of properly sizing the pylon can be both time consuming and wasteful.

A further drawback, given that the pylon is not longitudinally adjustable with respect to the tube clamp, is that there exists an inability to finely tune a conventional prosthetic limb. That is, if the practitioner miscalculates or misconstructs the prosthetic limb even by a fraction of an inch, there is no way to overcome the shortcomings in the prosthetic limb simply by making an adjustment between the pylon and the tube clamp. In this event, absent construction of new components, the person may be forced to live with an improperly fitting prosthetic limb.

A further drawback is evident upon comparison of FIGS. 2 and 3. In FIG. 2, the person 5 is properly fitted with a prosthetic limb. Yet, the duration of time during which the prosthetic limb will properly fit is necessarily limited. Existing prosthetic limbs may initially fit well but may not fit well after the person grows or shrinks. FIG. 3 shows such a situation. In FIG. 3, the person has grown and the prosthetic limb has become too short. Specifically, the prosthetic limb is shorter than the natural limb by an offset length OL. While not specifically shown, it is noted that the opposite is true when a person shrinks. In such a case, the initially properly sized prosthetic limb will become too long. These problems are most prevalent in the young and the elderly, respectively. Given the inability to adjust the effective length of the prosthetic limb, the practitioner will need to replace major components of the limb or even construct an entirely new prosthetic limb as the size of the person changes. Replacing major prosthetic componentry is expensive, both in materials and in the practitioner's time, and is also inconvenient.

The time, cost and inconvenience associated with replacements and adjustments of conventional prosthetic limbs may have the effect of encouraging infrequent visits to the practitioner. As the duration of time between visits increases, the prosthetic limb continues to fit worse and worse. In turn, the person may become dissatisfied with their prosthetic limb.

Thus there exists a need for modular prosthetic limb components that solve these and other problems.

SUMMARY OF THE INVENTION

The present invention relates to a system with modular components for forming a prosthetic limb, wherein the effective length of the limb is adjustable to accommodate changing needs of a particular person. The present invention is intended for use with conventional prosthetic components.

According to the present invention, several modular components are provided. One set of modular components comprise sleeve modules, or sleeves. Each sleeve has a body and two opposed ends. The ends each contain an internally threaded clamp. The sleeves can be constructed to any overall length. Spacer modules, or spacers, of several different overall lengths are also provided. Each spacer has a body and two opposed ends. Each end is externally threaded.

The sleeve modules and spacer modules can be used with several additional components, such as a receiver with a clamped end or externally threaded end, and also with a pyramidal adapter with either a clamped end or externally threaded end. A practitioner can construct a custom fit prosthetic limb by selected from the several of the above-noted modular components.

One advantage of the present invention is that the modules are twistable with respect to each other. Twisting the modules with respect to each other allows for the overall length of the prosthetic limb to be longitudinally adjusted and finely tuned to meet the needs of the person. The overall length of the prosthetic limb can be adjusted by amounts as small as a fraction of an inch.

Another advantage of the present invention is that the modules can be selectably interchanged with modules of a different size. Hence, when the need for adjustment is greater than the adjustment capabilities provided by twisting the components with respect to each other, a module of a more proper size can be quickly and easily interchanged for the less properly sized component. Then, the overall length can again be fine tuned by twisting the components with respect to each other to achieve the desired prosthetic limb length. Multiple sleeve modules and spacer modules are provided according to the present invention.

According to the present invention, even if a new component is required to make a longitudinal adjustment, the remainder of the components can remain in use. This is accomplished by swapping the module having a first length with a second module having a second length. This flexibility greatly reduces the hassle and cost associated with seeking adjustments to the length of prosthetic limbs. A person is therefore more likely to seek professional assistance at the first signs that their prosthetic limb may need readjustment. The person will have a more positive overall experience with their prosthetic limb when it remains at a proper length.

The benefits of the present invention are not conferred only upon the particular person with the prosthetic limb of the present invention. Rather, the practitioner and other people in need of prosthetic care will benefit as well. By allowing adjustments to be made quicker and easier, the practitioner will have more time to see and help even more people.

Other advantages, benefits, and features of the present invention will become apparent to those skilled in the art upon reading the detailed description of the invention and studying the drawings.

BRIEF DESCRIPTION OF THE DRAWINGS

FIG. 2 is a perspective view of a person with the conventional leg prosthesis setup of FIG. 1.

FIG. 3 is similar to FIG. 2, but shows the same conventional leg prosthesis setup after the person has grown.

FIG. 4 is a side view of a sleeve module of the present invention.

FIG. 5 is a cross-sectional view taken along line 5—5 in FIG. 4.

FIG. 4A is a side view of an alternative embodiment of the sleeve module of the present invention.

FIG. 5A is a cross-sectional view taken along line 5A—5A in FIG. 4A.

FIG. 6 is a side view of a spacer module of the present invention.

FIG. 7 is a cross-sectional view taken along line 7—7 in FIG. 6.

FIG. 6A is a side view of a spacer module of the present invention.

FIG. 7A is a cross-sectional view taken along line 7A—7A in FIG. 6A.

FIG. 10 is a side view of a receiver adapter with a clamped end.

FIG. 11 is a cross-sectional view taken along line 11—11 in FIG. 10.

FIG. 14 is a side view of a pyramidal adapter with a clamped end.

FIG. 15 is a cross-sectional view taken along line 15—15 in FIG. 14.

FIG. 19 is similar to FIG. 17, but shows a spacer module of a second size interchanged with the spacer module of a first size.

FIG. 20 is similar to FIG. 19, but shows a sleeve module of a second size interchanged with a sleeve module of a first size.

DETAILED DESCRIPTION OF THE PREFERRED EMBODIMENTS

Figure 1:
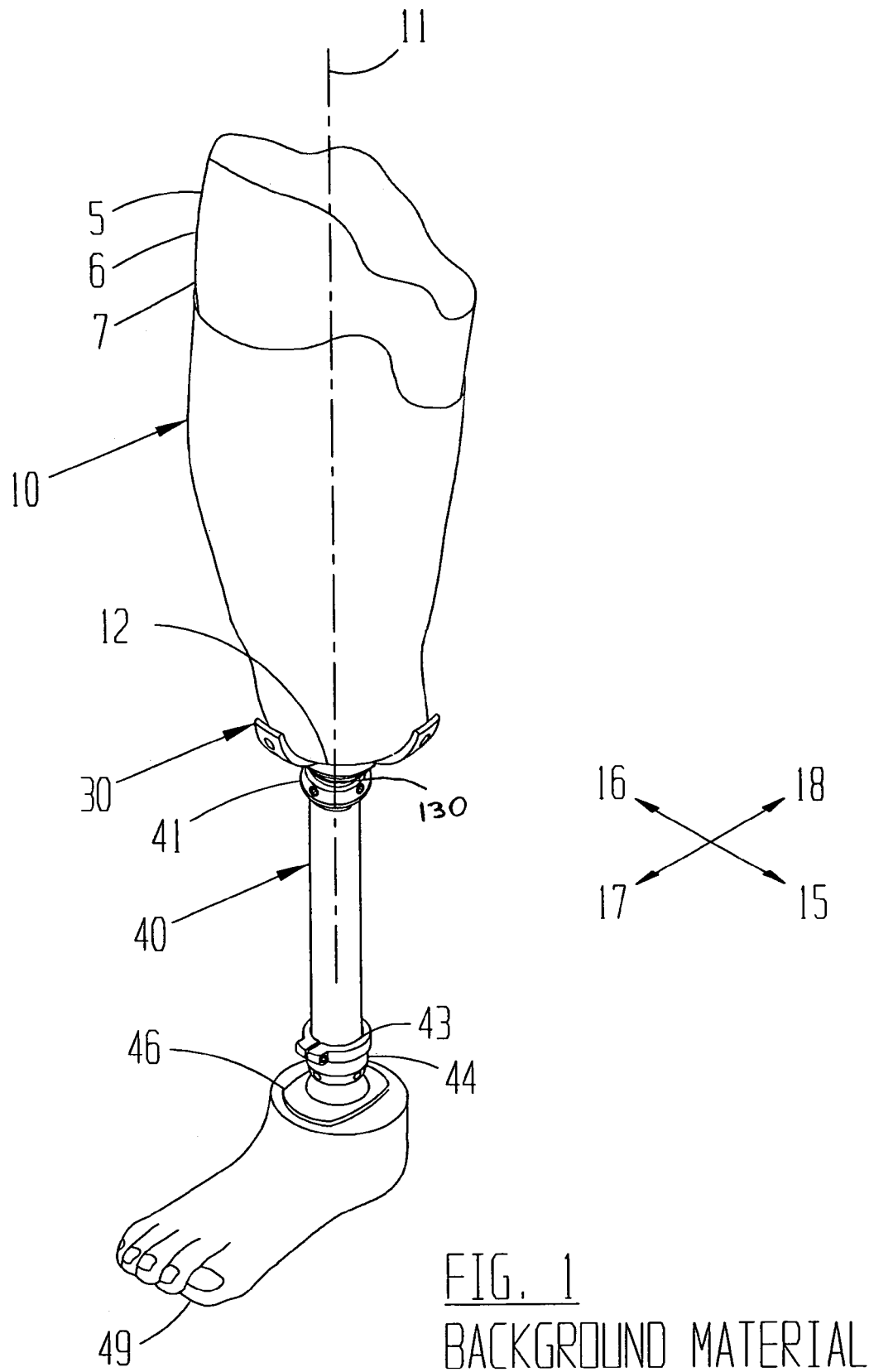
FIG. 1 is a perspective view of a conventional leg prosthesis setup.

While the invention will be described in connection with several preferred embodiments, it will be understood that it is not intended to limit the invention to those embodiments. On the contrary, it is intended to cover all alternatives, modifications and equivalents as may be included within the spirit and scope of the invention as defined by the appended claims.

Turning now to FIGS. 4 and 5, a first module 50 is provided. According to one aspect of the present invention, the module 50 can be a sleeve 60 or sleeve module. The sleeve 60 is preferably made of Titanium allow. However, other materials can be used without departing from the broad aspects of the present invention. The sleeve 60 has a first end 65. The sleeve 60 has a clamp 66 on the exterior surface of the first end 65 and is threaded with threads 67 on the interior surface of the first end. Opposed to the first end 65 is a second end 70. The second end 70 is similar to the first end 65, and comprises a clamp 71 in its exterior surface and is threaded with threads 72 on its interior surface. A body 75 exists between the first end 65 and the second end 70. The sleeve 60 has an overall length Gamma.

An alternative embodiment of the first module is shown in FIGS. 4A and 5A, and the alternative is shown with reference number 60A. Sleeve 60A has a first end 65A. The sleeve 60A has a clamp 66A on the exterior surface of the first end 65A and is threaded with threads 67A on the interior surface of the first end. Opposed to the first end 65A is a second end 70A. The second end 70A is similar to the first end 65A, and comprises a clamp 71A in its exterior surface and is threaded with threads 72A on its interior surface. A body 75A exists between the first end 65A and the second end 70A. The sleeve 60A has an overall length GammaA.

Figure 4B:
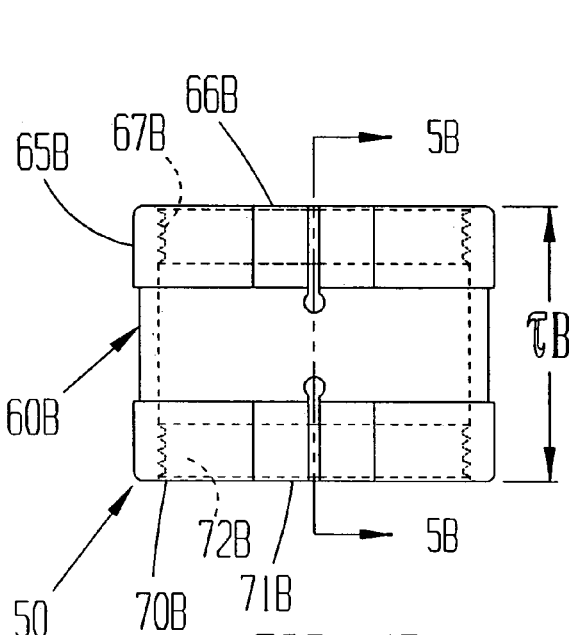
FIG. 4B is a side view of an alternative embodiment of the sleeve module of the present invention.
Figure 5B:
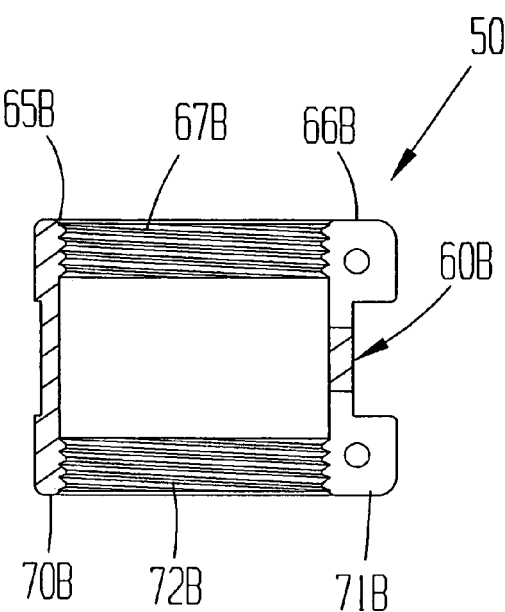
FIG. 5B is a cross-sectional view taken along line 5B—5B in FIG. 4B.

A further alternative embodiment of the first module is shown in FIGS. 4B and 5B, and the alternative embodiment is shown with reference numeral 60B. Sleeve 60B has a first end 65B. The sleeve 60B has a clamp 66B on the exterior surface of the first end 65B and is threaded with threads 67B on the interior surface of the first end. Opposed to the first end 65B is a second end 70B. The second end 70B is similar to the first end 65B, and comprises a clamp 71B in its exterior surface and is threaded with threads 72B on its interior surface. A body 75B exists between the first end 65B and the second end 70B. The sleeve 60B has an overall length GammaB.

Figure 4C:
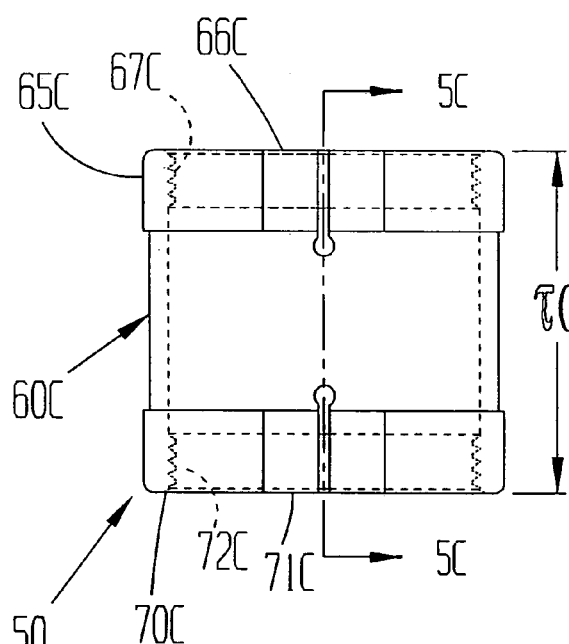
FIG. 4C is a side view of an alternative embodiment of the sleeve module of the present invention.
Figure 5C:
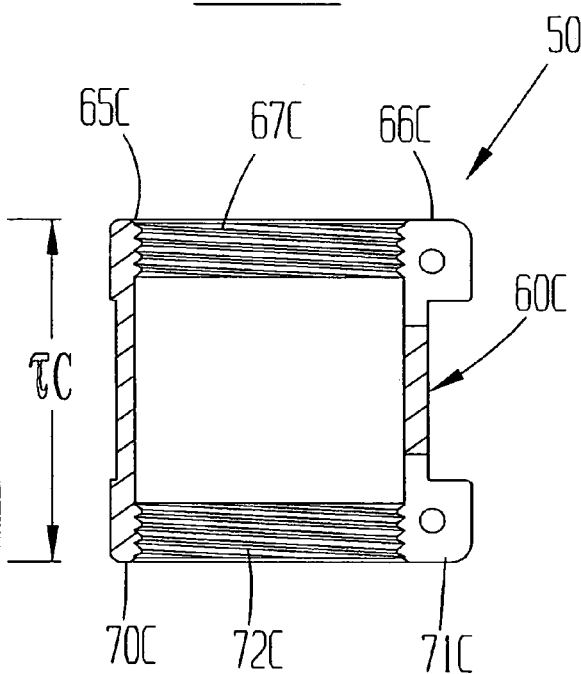
FIG. 5C is a cross-sectional view taken along line 5C—5C in FIG. 4C.

A still further alternative embodiment of the first module is shown in FIGS. 4C and 5C, and the alternative embodiment is shown with reference numeral 60C. Sleeve 60C has a first end 65C. The sleeve 60C has a clamp 66C on the exterior surface of the first end 65C and is threaded with threads 67C on the interior surface of the first end. Opposed to the first end 65C is a second end 70C. The second end 70C is similar to the first end 65C, and comprises a clamp 71C in its exterior surface and is threaded with threads 72C on its interior surface. A body 75C exists between the first end 65C and the second end 70C. The sleeve 60C has an overall length GammaC.

Even though four embodiments of the sleeve module 60 are described and shown, it is apparent that the present invention is not limited to those embodiments. Rather, sleeve modules of other lengths are also considered to be within the scope of the present invention.

Turning now to FIGS. 6 and 7, a second module 50 is provided. The second module is a spacer 80 or spacer module. The spacer is preferably made of Titanium allow. However, it may be made from other materials without departing from the broad aspects of the present invention. The spacer 80 has a first end 85. The first end 85 has an external surface 86 that is threaded with threads 87. Opposed to the first end 85 is a second end 90. The second end 90 has an external surface 91 that is threaded with threads 92. A body 95 is provided and is located between the first and second ends 85 and 90, respectively. The body 95 has a length. The spacer 80 has an overall length Epsilon.

An alternative embodiment of the second module is shown in FIGS. 6A and 7A, and the alternative embodiment is shown with reference numeral 80A. Spacer 80A has a first end 85A. The first end 85A has an external surface 86A that is threaded with threads 87A. Opposed to the first end 85A is a second end 90A. The second end 90A has an external surface 91A that is threaded with threads 92A. A body 95A is provided and is located between the first and second ends 85A and 90A, respectively. The body 95A has a length. The spacer 80A has an overall length EpsilonA.

Figure 6B:
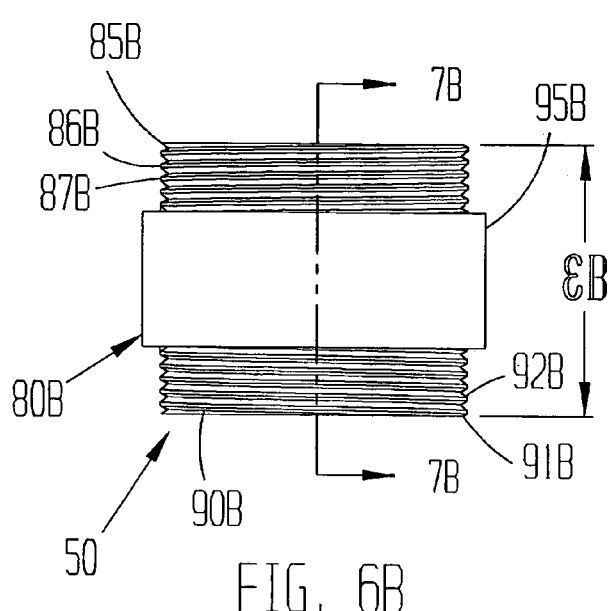
FIG. 6B is a side view of a spacer module of the present invention.
Figure 7B:
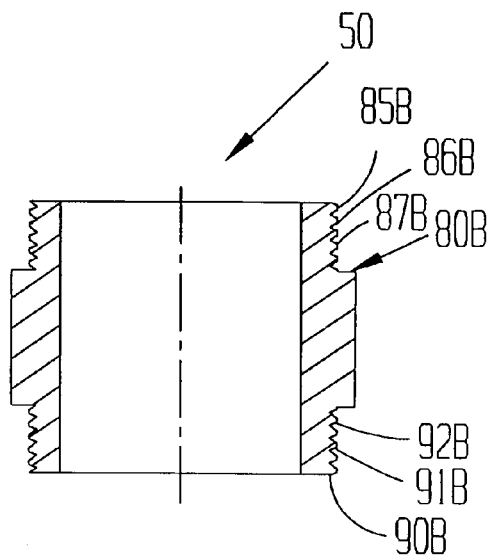
FIG. 7B is a cross-sectional view taken along line 7B—7B in FIG. 6B.

A further alternative embodiment of the second module is shown in FIGS. 6B and 7B, and the alternative embodiment is shown with reference numeral 80B. Spacer 80B has a first end 85B. The first end 85B has an external surface 86B that is threaded with threads 87B. Opposed to the first end 85B is a second end 90B. The second end 90B has an external surface 91B that is threaded with threads 92B. A body 95B is provided and is located between the first and second ends 85B and 90B, respectively. The body 95B has a length. The spacer 80B has an overall length EpsilonB.

Figure 6C:
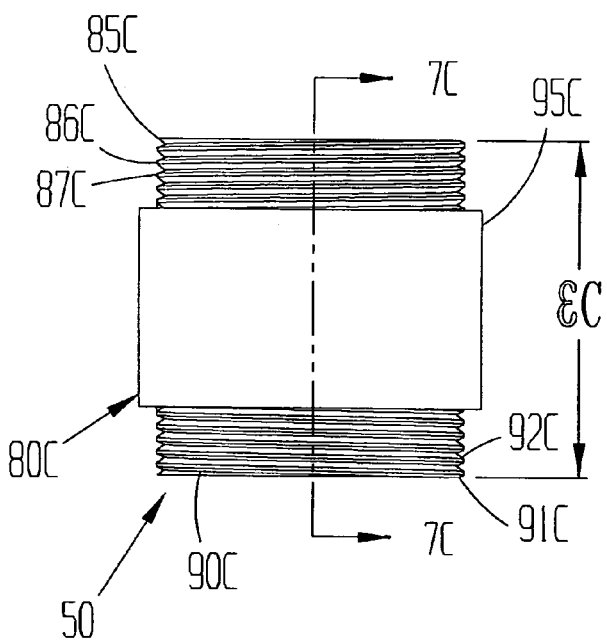
FIG. 6C is a side view of a spacer module of the present invention.
Figure 7C:
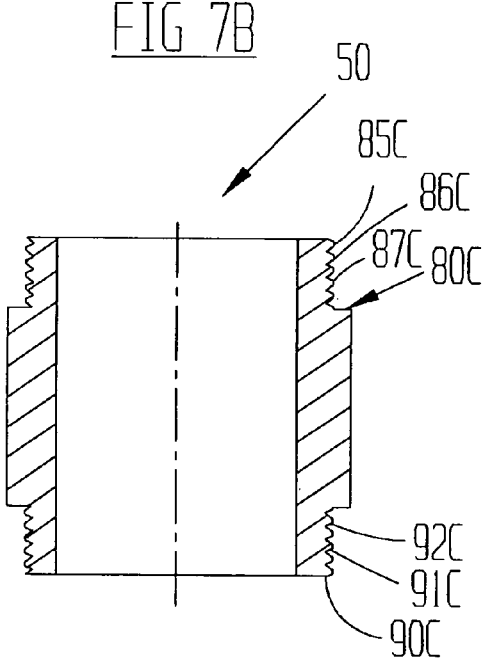
FIG. 7C is a cross-sectional view taken along line 7C—7C in FIG. 6C.

A still further alternative embodiment of the second module is shown in FIGS. 6C and 7C, and the alternative embodiment is shown with reference numeral 80C. Spacer 80C has a first end 85C. The first end 85C has an external surface 86C that is threaded with threads 87C. Opposed to the first end 85C is a second end 90C. The second end 90C has an external surface 91C that is threaded with threads 92C. A body 95C is provided and is located between the first and second ends 85C and 90C, respectively. The body 95C has a length. The spacer 80C has an overall length EpsilonC.

Figure 9:
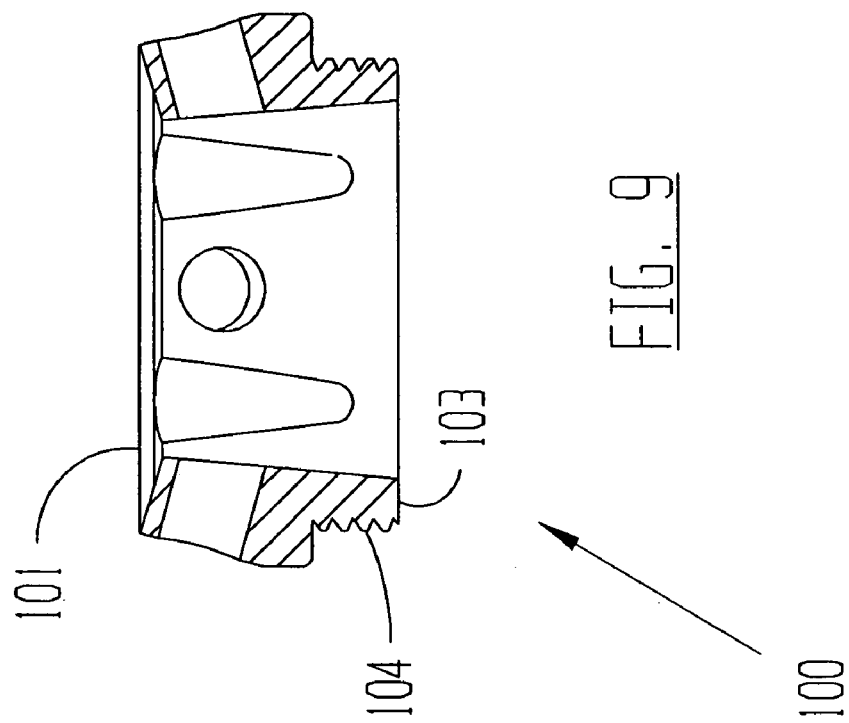
FIG. 9 is a cross-sectional view taken along line 9—9 in FIG. 8
Figure 8:
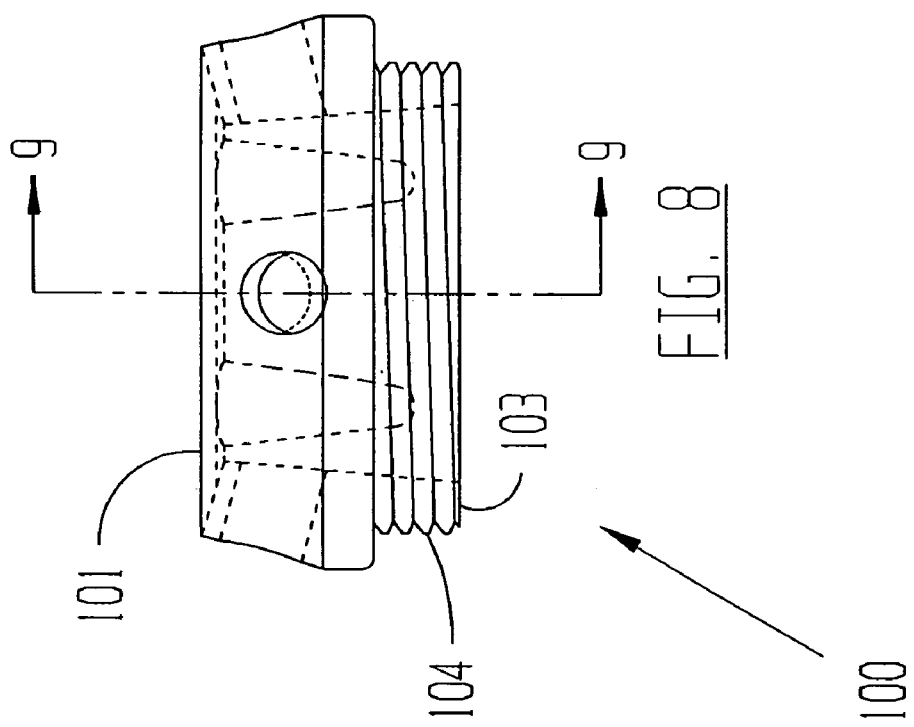
FIG. 8 is a side view of a receiver adapter with an externally threaded end.

A receiver adapter with externally threaded end 100 is provided, and is shown in FIGS. 8 and 9. The receiver adapter 100 is preferably made of Titanium allow. However, other materials can alternatively be used. The receiver adapter 100 has a receiver 101 at a first end. At the opposed end 103 is an external surface that is threaded with threads 104. The receiver 101 is adapted to receive a conventional pyramidal object. The receiver 101 has four sides. Each side has a threaded hole therethrough for receiving a screw. The screws can be selectively twisted into the respective holes to clamp onto a pyramidal object received within the receiver 101.

A receiver adapter with clamped end 110 is provided and is shown in FIGS. 10 and 11. The receiver adapter 110 is preferably made of Titanium allow. However, other material may alternatively be used. The receiver adapter 110 has a receiver 111 at a first end. At the opposed end 113 is a clamp 114, which is located on the external surface of end 113. The interior surface of the clamped end 113 is threaded with threads. The receiver 111 is adapted to receive a conventional pyramidal object. The receiver 111 has four sides. Each side has a threaded hole therethrough for receiving a screw. The screws can be selectively twisted into the respective holes to clamp onto a pyramidal object that is received within the receiver 111.

Figure 13:
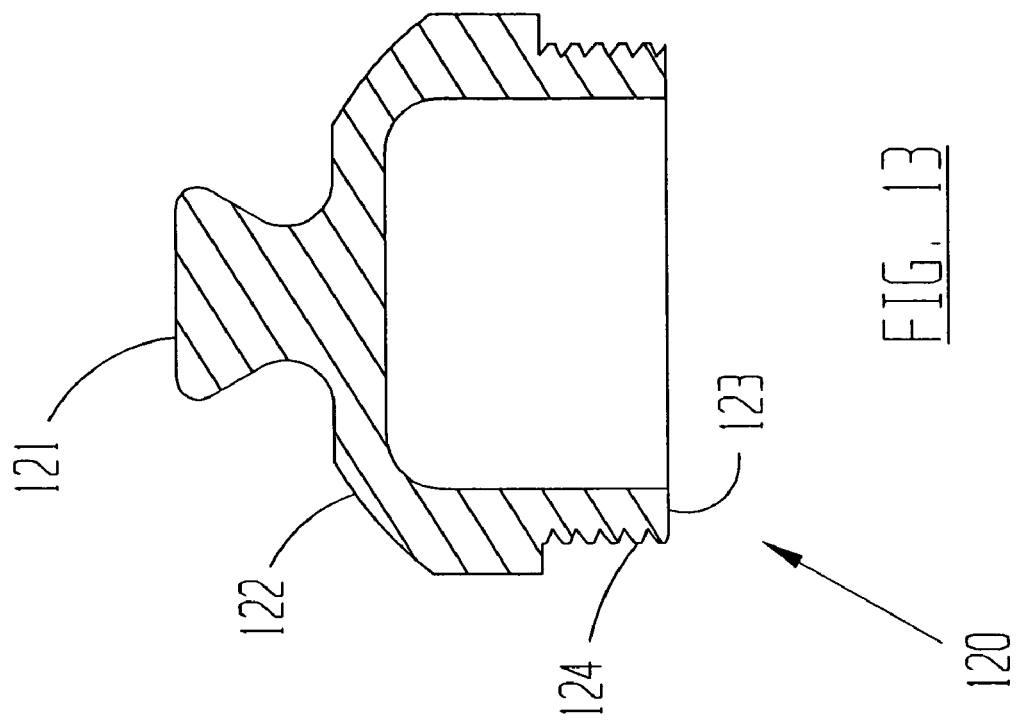
FIG. 13 is a cross-sectional view taken along line 13—13 in FIG. 12.
Figure 12:
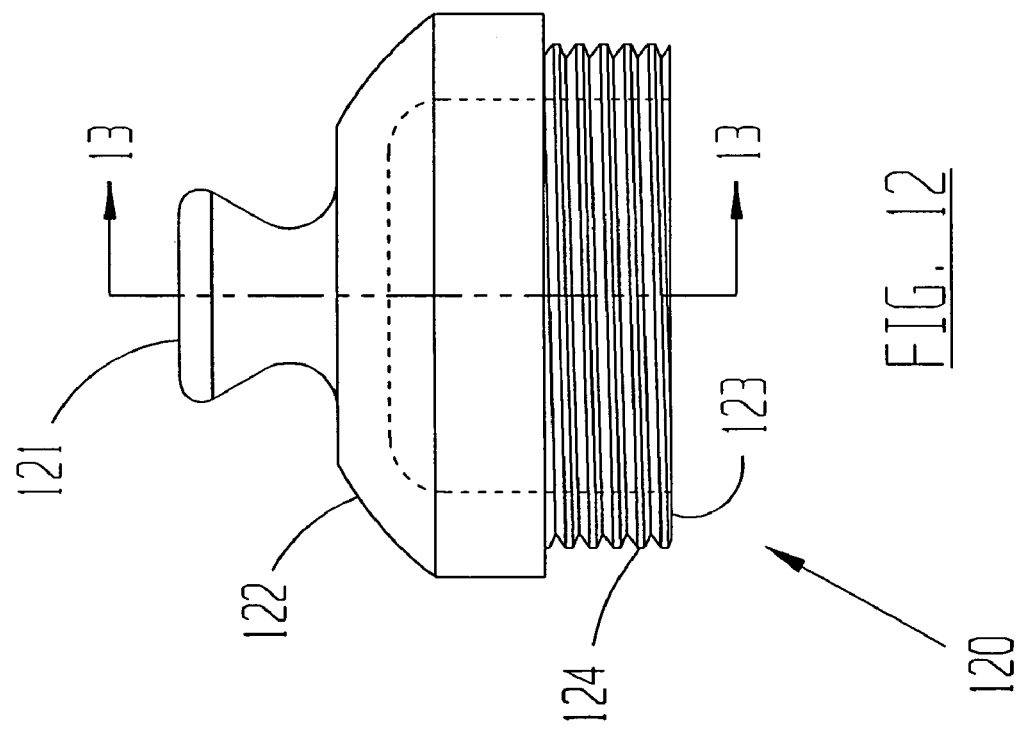
FIG. 12 is a side view of a pyramidal adapter with an externally threaded end.

Turning now to FIGS. 12 and 13, a pyramidal adapter with externally threaded end 120 is provided. The pyramidal adapter 120 is preferably made of Titanium allow. However, other materials may alternatively be used. The pyramidal adapter 120 has a first end comprising a pyramid 121. The pyramid 121 is preferably positioned centrally upon a dome 122. Opposed to the pyramid 121 is an externally threaded end 123 having threads 124 on the external surface.

A further prosthetic component is shown in FIGS. 14 and 15. In this regard, a pyramidal adapter with clamped end 130 is provided. The pyramidal adapter 130 is preferably made of Titanium allow. However, other materials may alternatively be used. The pyramidal adapter 130 has a first end comprising a pyramid 131. The pyramid 131 is preferably positioned centrally upon a dome 132. Opposed to the pyramid 131 is a clamped end 133. The clamped end 133 comprises a clamp 134 on the external surface, and has an internal surface that is threaded with threads 135.

Applicant notes that components 100, 110, 120 and 130 are provided for illustrative purposes, and the principles of the present invention may extend beyond these preferred embodiments.

The components shown and described herein can be interchangeably and adjustably connected together to create a prosthetic limb having the desired length and orientation. Several examples of how the components may be interchanged are provided. Yet, it is understood that the present invention is not limited to those embodiments.

Figure 16:
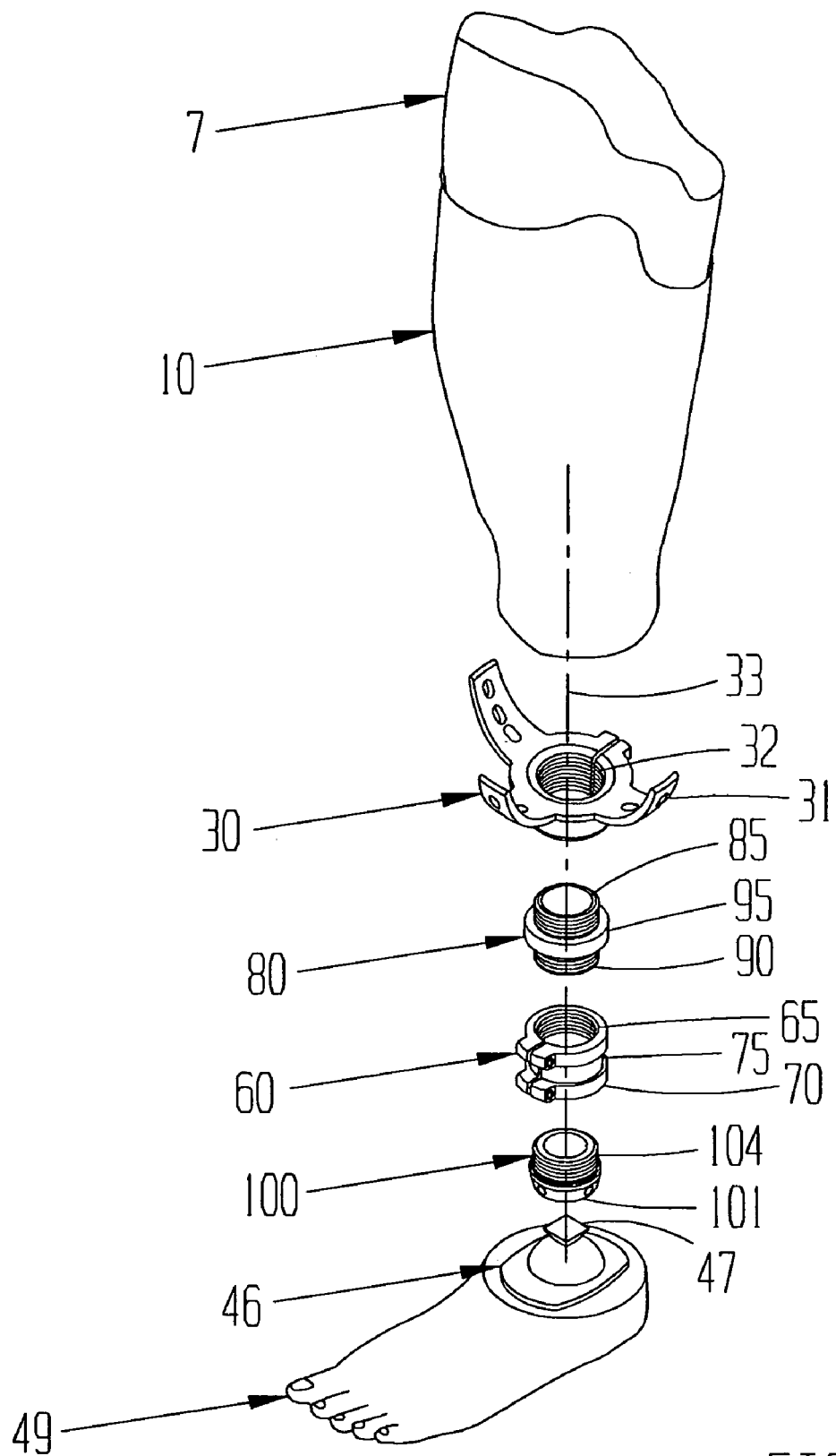
FIG. 16 is an exploded view of a preferred embodiment of the present invention.

One preferred set up comprising components of the present invention is shown in an exploded view in FIG. 16. As shown, a stump 7 with a conventional socket 10 is provided. A three prong adapter 30 having prongs 31 and an internally threaded end 32 and is adapted to be connected to the socket 10 in a conventional manner. A spacer module 80 is provided, and the first end 85 is positioned for being screwed into the internally threaded end 32 of the three prong adapter. Further, a sleeve module 60 is provided such that the first end 65 can be screwed onto the second end 90 of the spacer module 80. A receiver adapter with externally threaded end 100 is shown next, and is positioned such that the externally threaded end 103 can be threadably received within the second end 70 of the sleeve module 60. The receiver 101 is then able to clamp onto a foot adapter 46 with a pyramidal end 47. The foot adapter 46, in turn is then connected to the foot 49. It is shown that the bodies 75 and 90 of the sleeve module 60 and the spacer module 80, respectively, are alignable upon a single axis that is generally parallel to a longitudinal axis of the prosthetic limb. These components, due to being threadably connected, are capable of being longitudinally adjusted relative to each other by twisting them in opposite directions about the single axis.

Figure 17:
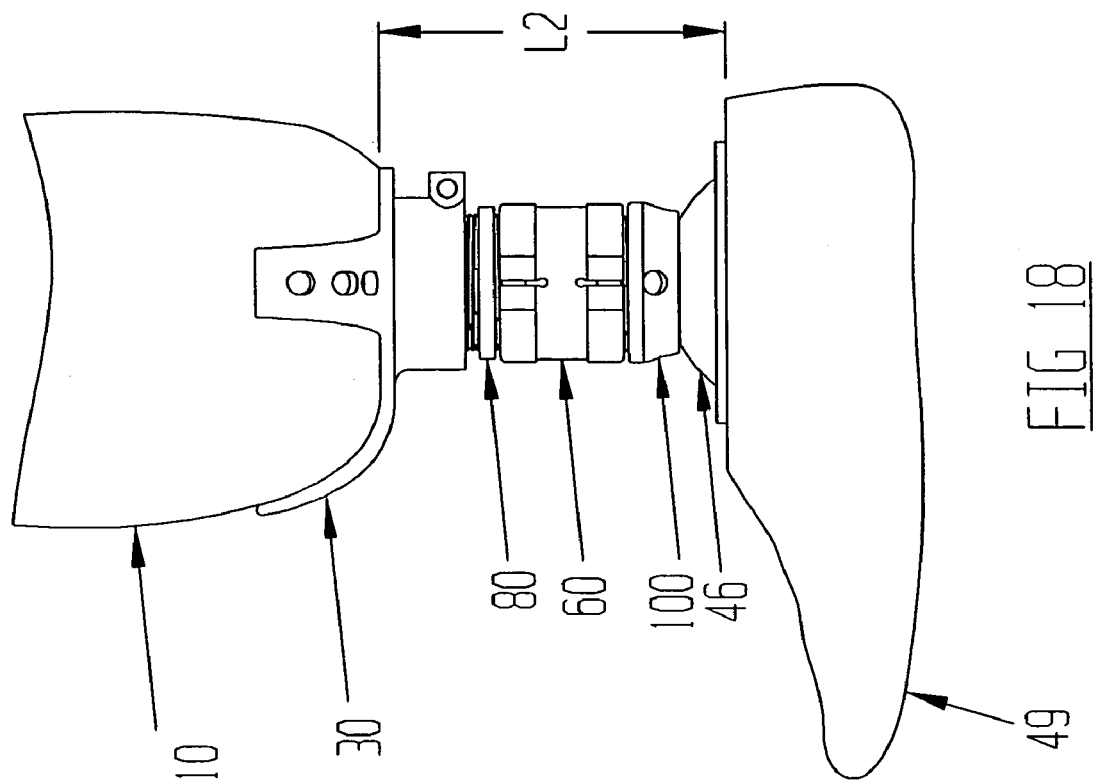
FIG. 17 is a side view of the preferred embodiment of the present invention shown in FIG. 16, but showing the prosthetic components assembled.

FIG. 17 shows a prosthetic limb comprising the components shown in FIG. 16. The components 30, 80, 60 and 100 are threadably connected to their respective adjacent components. Upon a closer look, it is seen that spacer 80 is threaded all the way into the internally threaded end 32 of the three prong adapter 30, such that the spacer and three prong adapter are fully engaged. Likewise, the sleeve module 60 fully receives the opposite end of the spacer 80. However, the threaded end of the receiver adapter 100 is not threaded completely into the sleeve. Rather, the receiver adapter 100 is unthreaded approximately one revolution from the sleeve 60. Selectably threading and unthreading a component changes the overall length of the prosthetic component. In this preferred embodiment, the prosthetic limb has a selected effective length L1.

Turning now to one intended use of the preferred invention, it is noted that in FIG. 17, the effective length L1 is the necessary length of the prosthetic limb such that the prosthetic limb will have a length equal to the natural limb. In this example, this fine tune adjustment was accomplished when the practitioner twisted the receiver adapter 100 one revolution out of full reception within the sleeve 60. It is noted that one full revolution is provided for illustrative purposes only. In practice, the components can be twisted with respect to each other by any fraction or multiple of one revolution.

Figure 18:
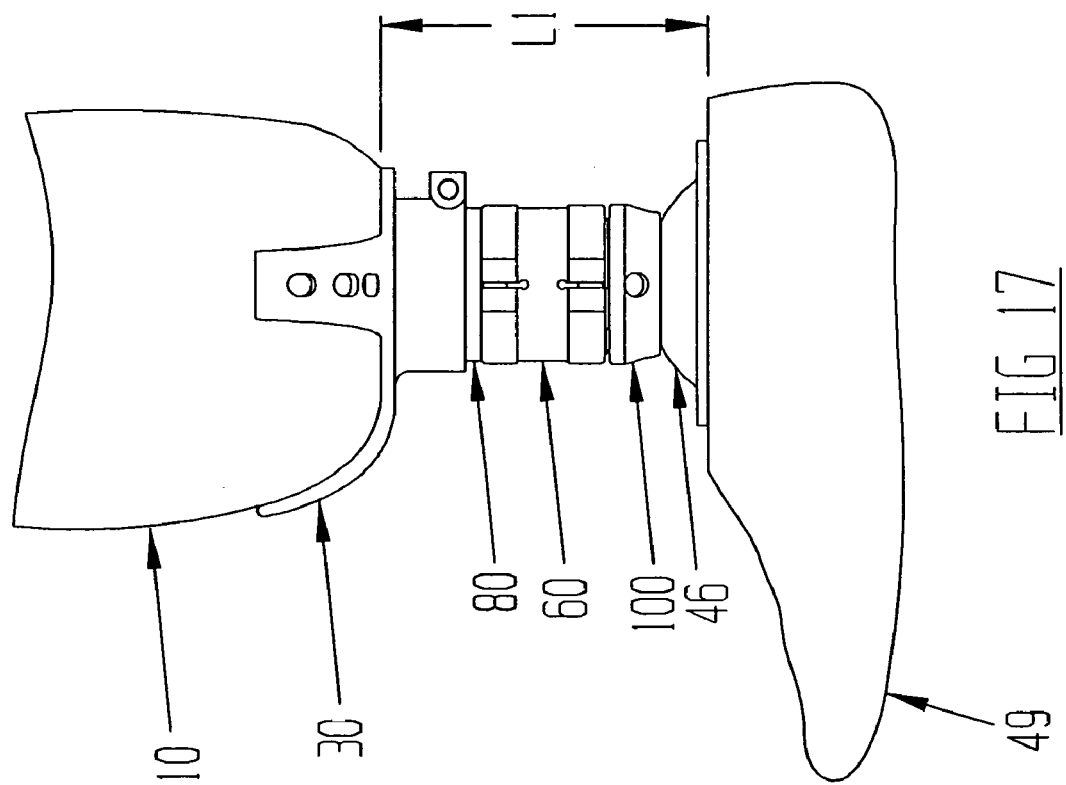
FIG. 18 is similar to FIG. 17, but shows some of the components partially unthreaded from each other in order to change the effective length of the prosthetic limb.

Principles of the present invention are further illustrated by way of comparison between FIGS. 17 and 18. The prosthetic limbs shown in FIGS. 17 and 18 both comprise identical components. However, the effective length L2 of the prosthetic limb shown in FIG. 18 is longer than the effective length L1 of the prosthetic limb shown in FIG. 17. This change if effective length is caused by selectably twisting the components out of full engagement with selected adjacent components. In particular, the first end of the spacer 80 is unthreaded approximately two revolutions out of full engagement with the three prong adapter 30. Further, the second end of the spacer 60 is unthreaded approximately one revolution out of the sleeve 80. This method of adjustment of the effective length of the prosthetic limb is useful when the overall required adjustment is relatively small.

Further, in accordance with the principles of the present invention, is the ability to swap modules 50 of one size with modules of a different size. Such principles are apparent upon comparison of FIGS. 18 and 19. One structural difference between the prosthetic limbs shown in the two figures is that the spacer 80 shown in FIG. 18 is replaced with spacer 80A in FIG. 19. Given that spacer 80A has a longer length Epsilon A than spacer 80 having length Epsilon, it is shown that the effective length L3 of the prosthetic limb shown in FIG. 19 is greater than the effective length L2 of the prosthetic limb shown in FIG. 18. Yet, no customizing of individual components is necessary to accomplish this change. Further, this change is accomplished merely by swapping a single component with another component. The effective length L3 of the prosthetic limb shown in FIG. 19 can be fine tuned be twisting some components as necessary either further into or out of their respective adjacent components.

FIG. 20 further demonstrates the flexibility of the present invention. FIG. 20 is similar to FIG. 19, but the sleeve module 60 has been replaced with larger sleeve module 60A. The effective length L4 of the prosthetic limb is increased replacing the first sleeve module 60 with the larger sleeve module 60A. Hence, it is apparent that the prosthetic limb can interchangeably be made longer as a person grows. Applicant notes that the overall effective length of the prosthetic limb can continue to increase if sleeves 60B or 60C and spacers 80B and 80C are interchanged for sleeve 60 or 60A and spacer 80 or 80A, respectively. It is noted that the practitioner can achieve the opposite effect by replacing a longer component with a relatively smaller like kind component.

Figure 21:
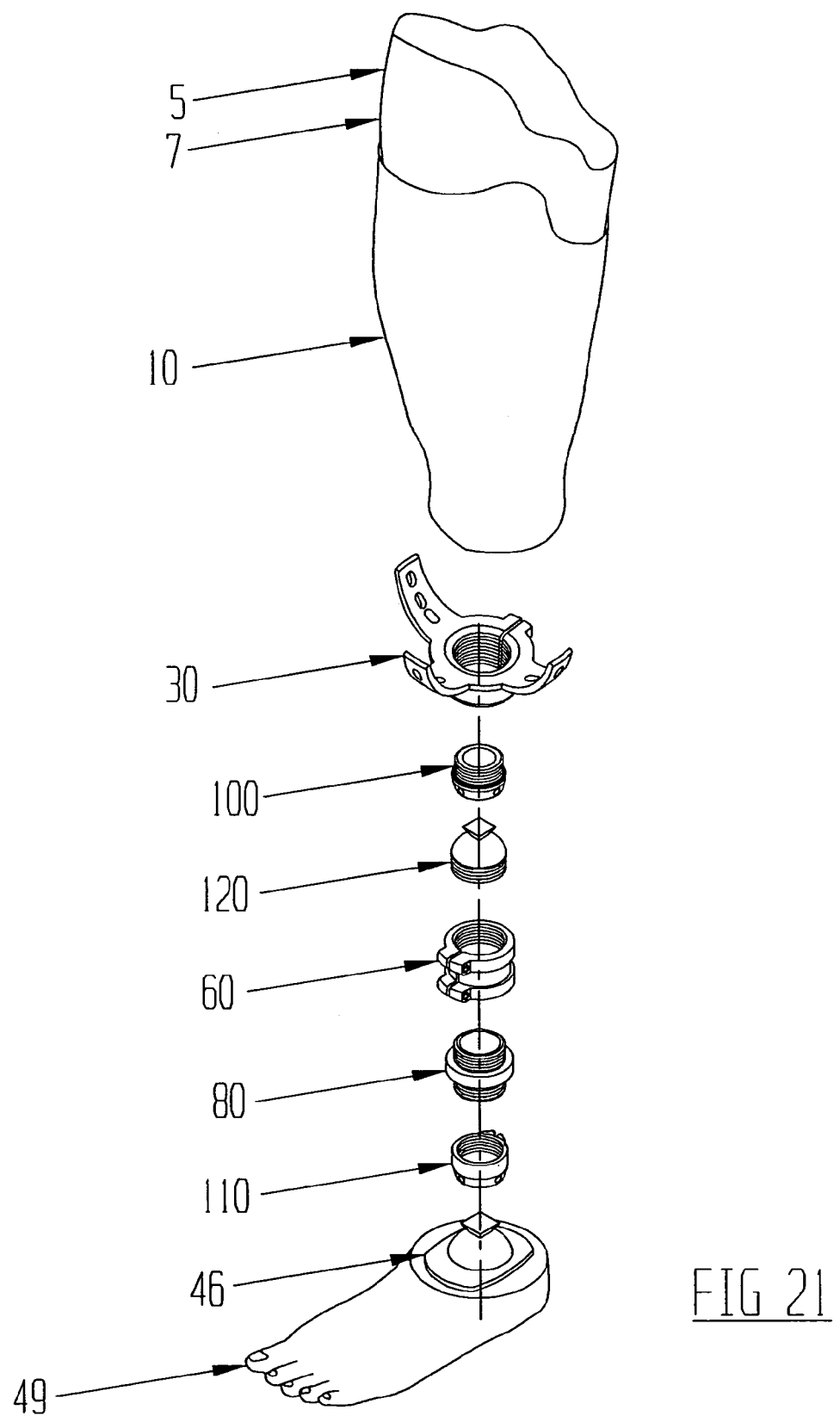
FIG. 21 shows an alternative embodiment of the present invention comprising an internally threaded three prong adapter, a receiver adapter with externally threaded end, a pyramidal adapter with externally threaded end, a sleeve module, a spacer module and a receiver adapter with clamped end.
Figure 22:
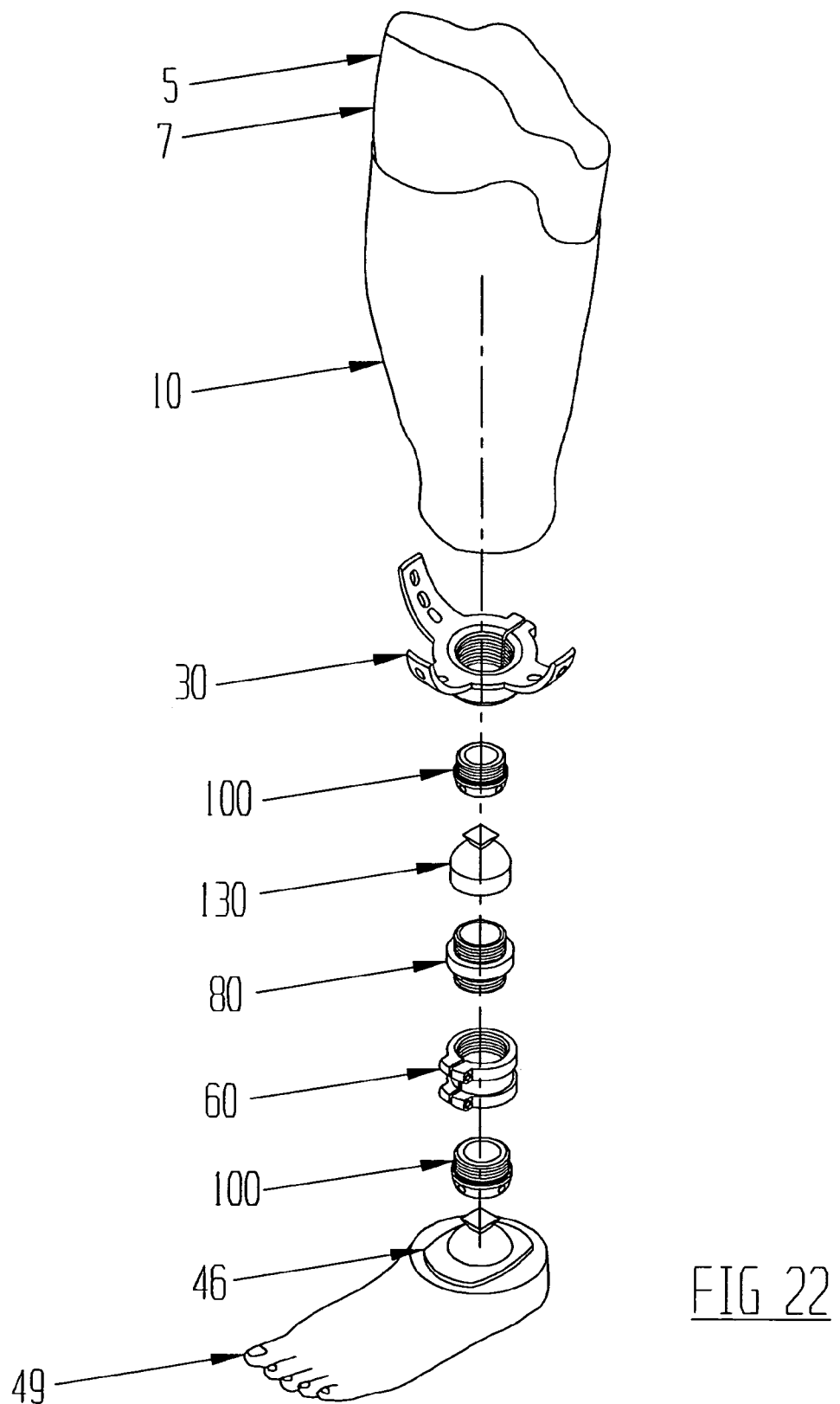
FIG. 22 shows an alternative embodiment of the present invention comprising an internally threaded three prong adapter, a receiver adapter with externally threaded end, a pyramidal adapter with clamped end, a spacer module, a sleeve module and a receiver adapter with an externally threaded end.
Figure 23:
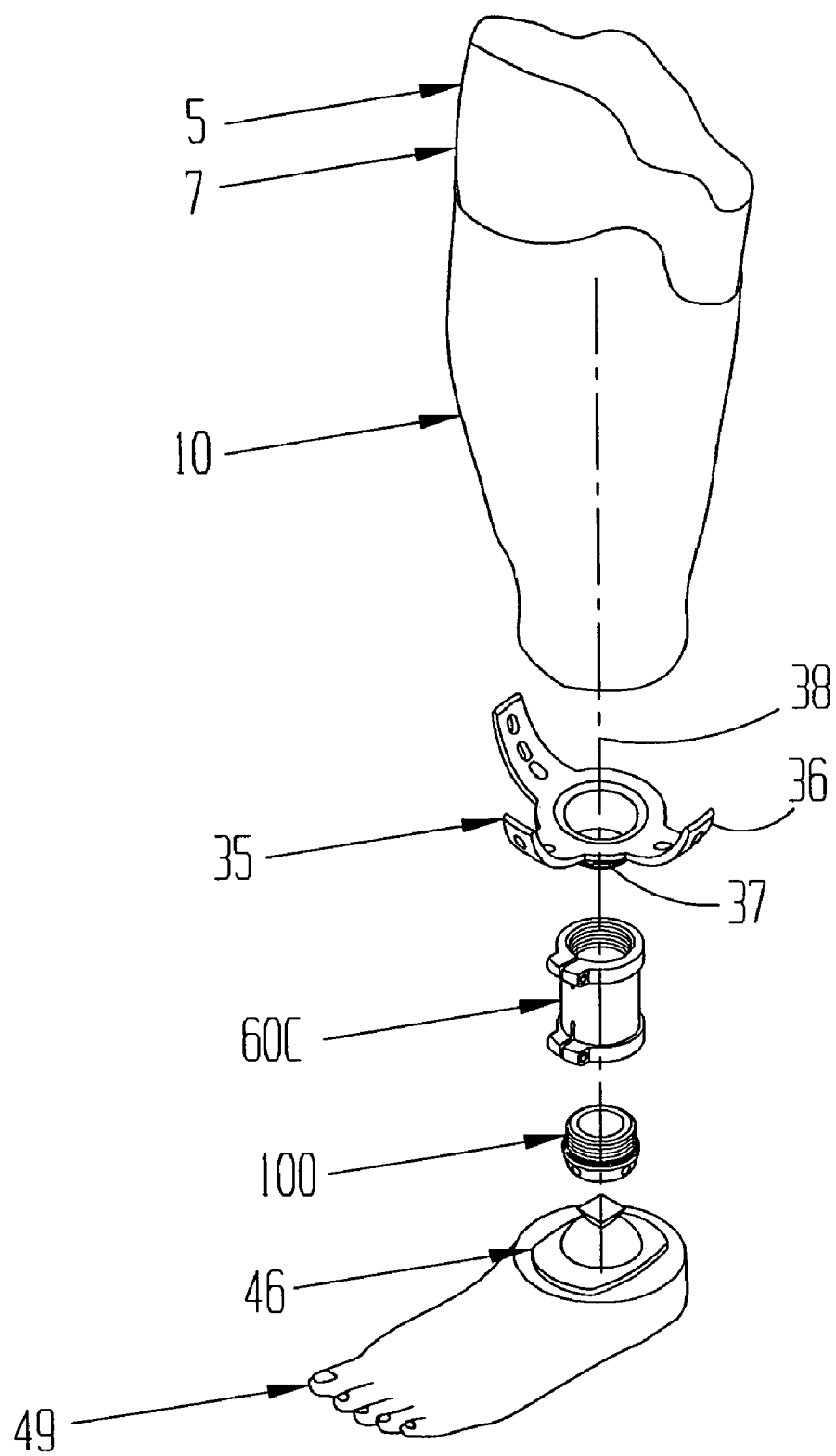
FIG. 23 shows an alternative embodiment of the present invention comprising an externally threaded three prong adapter, a sleeve module and a receiver adapter with externally threaded end.

FIGS. 21–23 further exemplify the principles of the present invention. In FIG. 20, a three prong adapter 30 is shown for connecting to the socket 10. A receiver adapter with an externally threaded end 100 is provided for connecting to the three prong adapter 30. Next, a pyramidal adapter with an externally threaded end 120 is provided for being angularly adjustably connected to the receiver adapter 120. A sleeve module 60 is provided for connecting to the pyramidal adapter 120. A spacer module 80 is provided for being connected to the sleeve module 60. A receiver adapter with externally threaded end 110 is also provided. The receiver adapter 110 can be connected to a foot adapter 46, which in turn is connectable to a prosthetic foot 49. The receiver adapter 100 and the pyramidal adapter 120 can be angularly adjustably connected to each other. Further, given that these components are threadably connected to their adjacent components, the receiver adapter 100 and the pyramidal adapter 120 can be connected into any rotational alignment with respect to those adjacent components.

FIG. 22 shows yet another prosthetic limb configuration employing the principles of the present invention. In this preferred embodiment, the components are in the following configuration: a three prong adapter 30 connectable to a receiver adapter with an externally threaded end 100, which is connectable to a pyramidal adapter with clamped end 130, which is connectable to a spacer module 80, which is connectable to a spacer module 60, which is connectable to a receiver adapter with an externally threaded end 100, which is connectable to a foot adapter 46 that is connected to a prosthetic foot 49.

Still another preferred embodiment is shown in FIG. 23. In this figure, the prosthetic limb has the following configuration: a three prong adapter 35 with external threads 37, the three prong adapter 35 being connectable to a relatively large sleeve module 60C, which is connectable to a receiver adapter with externally threaded end 100, which is connectable to a foot adapter 46 that is connected to a foot. FIG. 23 illustrates the ability to construct a fully adjustable and fine tunable prosthetic limb with only a limited number of components.

It is apparent that the number of possible configurations embodying the principles of the present invention is numerous, and that it is impractical to show in detail all of the numerous possible configurations. Rather, several preferred embodiments have been provided and serve as to demonstrate the principles of the present invention.

Turning now to the setup and use of the present invention, it is noted that the modules 50 of the present invention are capable of being used with other prosthetic components not shown herein. For example, angular and offset alignment devices presently exist, and can readily be incorporated into a system comprising the principles of the present invention.

In order to construct a prosthetic limb, the practitioner will first need to observe the socket 10 in order to determine the shape and orientation of the end 12 of the socket. In some cases, the prosthetic limb will need to incorporate angular and/or offset alignment devices. If so, the proper devices will be selected first. Next, a means for connecting the prosthetic limb to the socket 10 will be selected and the prosthetic foot 49 will be selected. Given that the practitioner knows the overall effective length required, and given that the practitioner knows the length of the selected components, the practitioner will be able to estimate the necessary length of the remaining components yet to be selected. The practitioner then can select modules 50 as necessary to interconnect with the previously selected components.

Next, the practitioner assembles the selected components. If the effective length of the assembled prosthetic limb is not close to the length of the natural limb, the modules 50 can be swapped with modules of a more appropriate length.

After the practitioner determines and incorporates the properly sized components, the practitioner then fine tunes the effective length of the prosthetic limb by selectably twisting the components towards or away from full engagement with the respective adjacent components. The clamps can then be tightened to lock the prosthetic components in place.

It is noted that offset alignment devices and angled alignment devices may need to be in a particular rotational orientation relative to a longitudinal axis of the prosthetic limb. Due to the rotational and threaded connectivity of the components provided, such a situation is not an obstacle. Rather, any offset alignment devices and angled alignment devices that are incorporated into the prosthetic limb are simply rotated or twisted with respect to their adjacent components until the desired rotational orientation is achieved.

The effective length of the prosthetic limb can be easily modified by simply loosening a clamp, and then either threading a first component either further towards or away from full engagement with its adjacent component, as appropriate. Yet, at some point, the required adjustment will exceed the adjustment capabilities provided by twisting the components relative to each other. In this case, a module 50 of a first size can be easily swapped with a module of a second size to obtain the proper effective length of the prosthetic limb.

It is noted that the modular aspects of the present invention allows the practitioner to make a custom fit prosthetic limb without the need for individually made custom components.

Thus it is apparent that there has been provided, in accordance with the invention, modular prosthetic limb components that fully satisfy the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A prosthetic limb comprising:
   A. a first prosthetic component connectable to a socket;
   B. a sleeve module with a main body connected to said first prosthetic component, said sleeve module having a length and a first end and a second end, a first slit being along said length at said first end and a second slit along said length at said second end, said sleeve module further having an internal surface with threads and an external surface with a first clamp at said first end and a second clamp at said second end;
   C. a spacer module with a main body having an interior surface and an exterior surface with threads for being connected to said threads of said internal surface of said sleeve module; and
   D. a second prosthetic component connected to said spacer module and adapted to be connected to a prosthetic foot,
   wherein said prosthetic limb has an adjustable effective length and said effective length is adjusted by selectively twisting said spacer module one of towards or away from full engagement with said sleeve module, and
   wherein said clamp secures said sleeve module onto said spacer module.

2. The prosthetic limb of claim 1 wherein said effective length of said prosthetic limb is further adjustable by:
   A. selectively twisting said sleeve module one of towards or away from full engagement with said first prosthetic component; and
   B. selectively twisting said spacer module one of towards or away from full engagement with said second prosthetic component.

3. The prosthetic limb of claim 1 wherein said sleeve module has a first selected length and the effective length of said prosthetic limb can be adjusted by interchanging a second sleeve module having a second length for said sleeve module having a first selected length.

4. The prosthetic limb of claim 1 wherein said spacer module has a first selected length and the effective length of said prosthetic limb can be adjusted by interchanging a second spacer module having a second length for said spacer module having a first length.

* * * * *